US008257748B2

(12) United States Patent
Pickens et al.

(10) Patent No.: US 8,257,748 B2
(45) Date of Patent: Sep. 4, 2012

(54) CALCIUM HYPOCHLORITE COMPOSITIONS

(75) Inventors: Stanley R. Pickens, Monroeville, PA (US); Robert B. Simmons, Wadsworth, OH (US)

(73) Assignee: PPG Industries Ohio, Inc., Cleveland, OH (US)

( * ) Notice: Subject to any disclaimer, the term of this patent is extended or adjusted under 35 U.S.C. 154(b) by 252 days.

(21) Appl. No.: 12/551,591

(22) Filed: Sep. 1, 2009

(65) Prior Publication Data

US 2011/0052724 A1    Mar. 3, 2011

(51) Int. Cl.
*A01N 59/08*    (2006.01)
*A01N 59/06*    (2006.01)
*C02F 1/76*     (2006.01)
*A61K 33/14*    (2006.01)
*C01B 11/06*    (2006.01)

(52) U.S. Cl. ........................................ 424/665; 252/175
(58) Field of Classification Search .................. None
See application file for complete search history.

(56) References Cited

U.S. PATENT DOCUMENTS

| 2,963,440 | A |   | 12/1960 | Robson |
| 3,234,141 | A | * | 2/1966  | Robson ................ 252/186.44 |
| 3,560,396 | A |   | 2/1971  | Robson |
| 3,639,284 | A |   | 2/1972  | Long et al. |
| 3,793,216 | A |   | 2/1974  | Dychdala et al. |
| 3,953,354 | A |   | 4/1976  | Faust |
| 4,048,351 | A |   | 9/1977  | Saeman et al. |
| 4,594,091 | A |   | 6/1986  | Girvan |
| 4,747,978 | A |   | 5/1988  | Loehr et al. |
| 4,965,016 | A |   | 10/1990 | Saitoh et al. |
| 5,049,385 | A |   | 9/1991  | Wiedrich et al. |
| 5,478,482 | A |   | 12/1995 | Jones et al. |
| 5,514,287 | A |   | 5/1996  | Jones et al. |
| 5,674,429 | A |   | 10/1997 | Lachocki et al. |
| 5,676,844 | A |   | 10/1997 | Girvan |
| 7,045,077 | B2 |  | 5/2006  | Garris |
| 2008/0067468 | A1 | * | 3/2008 | Pickens et al. ............... 252/178 |

FOREIGN PATENT DOCUMENTS

WO    WO 99/61376    12/1999

OTHER PUBLICATIONS

Kogel et al. Industrial Minerals & Rocks: Commodities, Markets, and Uses. (2006) 7th edition, p. 256.*

* cited by examiner

*Primary Examiner* — David J Blanchard
*Assistant Examiner* — Peter Anthopolos
(74) *Attorney, Agent, or Firm* — Irwin M. Stein; Linda Pingitore

(57) ABSTRACT

Described are compositions containing a mixture of (a) particulate calcium hypochlorite and (b) an amount of aluminum hydroxide that is sufficient to increase the UN-burn time of the composition by a factor of at least 2.5 compared to that of the calcium hypochlorite, the composition having an available chlorine content of at least 35 weight percent. Further described are solid compositions of (a) granular calcium hypochlorite having a UN Packing Group oxidizer classification of II, and (b) an amount of aluminum hydroxide such that the composition is classified as a Packing Group III Division 5.1 oxidizer or as a non-Division 5.1 oxidizer, the composition having an available chlorine content of at least 40 weight percent. Further described are formed articles prepared from the above-described compositions.

22 Claims, No Drawings

CALCIUM HYPOCHLORITE COMPOSITIONS

FIELD OF THE INVENTION

This invention relates to calcium hypochlorite compositions. In particular, this invention relates to calcium hypochlorite compositions having longer UN-burn times than that of unmodified calcium hypochlorite. More particularly, this invention relates to calcium hypochlorite compositions and formed articles prepared from such compositions, e.g., tablets, having a lower oxidizer hazard classification than unmodified calcium hypochlorite.

BACKGROUND OF THE INVENTION

Recreational and commercial water systems, as well as natural bodies of water, e.g., ponds, are subject to contamination from the presence and growth of microbial species, e.g., algae, pathogenic bacteria and fungi. The sanitizing of standing or recirculating water systems often involves introducing a hypochlorite anion donor material, such as calcium hypochlorite, into the water system to establish therein a desired level, e.g., a sanitizing amount, of free available chlorine (FAC). The introduction of sanitizing amounts of free available chlorine into a water system serves to eradicate or control deleterious amounts of microbial species that are present in the water comprising the water system. Sanitation of water contacted by humans and animals is required because exposure to unsanitized or inadequately sanitized water that contains deleterious amounts of pathogenic bacteria, fungi, viruses, protozoa, etc can lead to the development of infection or disease.

Recreational bodies of water, e.g., swimming pools, hot tubs, spas, etc are generally treated with chlorine-containing sanitizers so as to contain free available chlorine (FAC) in amounts of from 1 to 3 parts FAC per million parts of water [ppm, (sometimes reported as milligrams per Liter, mg/L)]. Water having an FAC content in amounts of greater than 10 ppm (generally in the range of hundreds to thousands of mg/L) can be used to sanitize surfaces or articles to which it is applied, e.g., surfaces of equipment or tables used for the preparation of food. Free available chlorine can be established in an aqueous system by adding regularly a source of hypochlorous acid (HOCl) or hypochlorite anion (ClO$^-$), e.g., calcium hypoochlorite, to the water comprising the aqueous system.

Calcium hypochlorite is a material that is regarded by the transportation industry as being an oxidizer, i.e., a material that can enhance the combustion of organic materials by providing oxygen for combustion. In accordance with U.S. Department of Transportation (DOT) regulations; namely, Title 49, Code of Federal Regulations (CFR), part 173, section 127, paragraph (a), subparagraph (1), [49 CFR §173.127 (a)(I)], calcium hypochlorite is categorized as a Division 5.1 oxidizer. More particularly, it is classified as a Packing Group II oxidizer material [49 CFR §172.101 and §173.127(b)(ii)].

The transport of a material categorized as a Division 5.1 oxidizer requires the use of special precautions, which can include the use of special containers. Moreover, materials categorized by the United Nations (specifically the Committee of Experts on the Transportation of Dangerous Goods) or by the US DOT as Division 5.1 oxidizers are generally also classified as oxidizers with reference to storage. See, for example, NFPA (National Fire Protection Association) 430 Code for the Storage of Liquid and Solid Oxidizers. The storage of solid oxidizers can therefore require separate free standing storage facilities and/or special sprinkler systems. Further, the amount of an oxidizer that is permitted to be stored in one location can also be limited. Hence, the requirements for storing and/or shipping calcium hypochlorite (in NFPA oxidizer classes 2 or 3) can involve a substantial cost premium.

It has been proposed to lower the oxidizer classification of calcium hypochlorite by blending certain inorganic water-soluble hydrated materials, such as magnesium sulfate heptahydrate, with the calcium hypochlorite. It has been observed however that when hydrated inorganic water-soluble materials are blended with calcium hypochlorite, the resultant blend is more susceptible to premature decomposition of the calcium hypochlorite during storage.

It would, therefore, be desirable to develop calcium hypochlorite compositions (and formed articles prepared from such compositions) that are not susceptible to premature decomposition during storage, and that are classified as a DOT Packing Group III Division 5.1 oxidizer, more desirably as a DOT non-Division 5.1 oxidizer. It is similarly desirable to have such compositions wherein the storage oxidizer hazard rating, e.g., the NFPA oxidizer class, is reduced. It would also be desirable that such calcium hypochlorite compositions and articles prepared from such compositions have an FAC content that is at least sufficient to allow its practical use in the batch and/or continuous sanitization of water systems, e.g., standing or recirculating water systems, such as a swimming pool, spa, hot tub, cooling tower water, evaporative condenser, etc.

DESCRIPTION OF THE INVENTION

The present invention provides a solid composition consisting essentially of a mixture of (a) calcium hypochlorite, e.g., hydrated calcium hypochlorite, and (b) an amount of aluminum hydroxide that is sufficient to increase the UN-burn time of the composition, by a factor of at least 2.5, as compared to that of calcium hypochlorite, said composition having an available chlorine content of at least 35 percent.

Also provided is a solid composition consisting essentially of a mixture of (a) granular calcium hypochlorite having a UN Packing Group oxidizer classification of II and (b) an amount of aluminum hydroxide such that the composition is classified as a Packing Group III Division 5.1 oxidizer or as a non-Division 5.1 oxidizer, said composition having an available chlorine content of at least 40 weight percent.

DETAILED DESCRIPTION OF THE INVENTION

For purposes of this specification (other than in the operating examples), unless otherwise indicated, all numbers expressing quantities and ranges of materials, physical properties, process conditions, etc are to be understood as modified in all instances by the term "about". Accordingly, unless indicated to the contrary, the numerical parameters set forth in this specification and attached claims are approximations that can vary depending upon the desired results sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Further, as used in this specification and the appended claims, the singular forms "a", "an" and "the" are intended to include plural referents, unless expressly and unequivocally limited to one referent.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements, including that found in the measuring instrument. Also, it is to be understood that any numerical range recited in this specification is intended to include all sub-ranges subsumed therein. For example, a range of "1 to 10" is intended to include all sub-ranges between and including the recited minimum value of 1 and the recited maximum value of 10, i.e., a range having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

As used in the following description and claims, the following terms have the indicated meanings:

The term "at least a DOT Packing Group III Division 5.1 classification" (or a term of like import) means that the indicated material or composition is classified as a DOT Packing Group III Division 5.1 material or is classified as a non-Division 5.1 oxidizer.

The term "hydrated calcium hypochlorite" means calcium hypochlorite having from 5.5 to 16 weight percent water, e.g., as bound water or as water of hydration. See, calcium hypochlorite, hydrated (UN #2880) in 49 CFR 172.101. The term "unmodified calcium hypochlorite" means solid calcium hypochlorite as synthesized which has not been modified by the addition of modifying amounts of "added" materials, such as inorganic metal salts, oxides, etc. The term "modifying amount", as used for example in the definition of unmodified calcium hypochlorite, means that the amount of added material is sufficient to significantly effect the free available chlorine content of the calcium hypochlorite. An amount of less than 1 weight percent is generally considered not to be a modifying amount.

The term "dry calcium hypochlorite" means calcium hypochlorite having less than 5.5 weight percent water, e.g., as bound water or as water of hydration.

The term "calcium hypochlorite" means calcium hypochlorite having an unspecified amount of bound water or water of hydration, and includes hydrated calcium hypochlorite and dry calcium hypochlorite.

The term "formed article" means an article that is formed, e.g., by compaction, into a shaped form, e.g., a tablet or other shaped form, from a particulate, e.g., granular, material.

The term "water-soluble" means that the indicated material is substantially soluble in water at ambient temperatures, e.g., temperatures in the range of 20° C. (68° F.) to 25° C. (77° F.).

The term "compatible", as used in connection with compatible inorganic salt material blended with calcium hypochlorite, means that the indicated material does not cause a significant, e.g., readily discernible, increase in the decomposition rate or lower the self-accelerating decomposition temperature of calcium hypochlorite.

The term "inert", as used for example in connection with the inorganic salt that may be blended with the particulate calcium hypochlorite, means that the indicated inorganic salt does not affect substantially the shelf life of the calcium hypochlorite composition of the present invention (or of articles formed from that composition), or the SADT (self accelerating decomposition temperature) of such a calcium hypochlorite composition (or of articles formed from that composition).

The terms "added", "mixed" or "blended", as used for example in connection with aluminum hydroxide or inorganic salt added to or blended with or mixed with particulate calcium hypochlorite, means that the indicated material has been physically combined with already synthesized calcium hypochlorite and is not intended to refer to any by-product material(s), e.g., inorganic salts, that may inherently be present in or with a calcium hypochlorite product as a result of the manufacturing process used to synthesize that calcium hypochlorite product. The terms "added", "mixed" or "blended" refer to material(s) that are physically combined, added to or blended with already synthesized calcium hypochlorite subsequent to its formation, such as for example during the physical steps of collecting, drying, sizing, packing, etc of the synthesized calcium hypochlorite. The term "mixture", "admixture", "blend" or terms of like import, as used for example in connection with the blend of calcium hypochlorite and aluminum hydroxide described in this description, means that the mixture, admixture or blend comprises a physical intermingling of distinct particles.

The term "appended", as used for example in connection with the added inorganic salt appended to the particles of the particulate calcium hypochlorite means that the added inorganic salt is not distributed internally or within the particles, e.g., granules, of the calcium hypochlorite, but is physically associated with and external to the particles, e.g., compacted granules, of the calcium hypochlorite.

The term "UN-burn time" means the average burn time recorded for a sample of 24 grams of a calcium hypochlorite composition and 6 grams of dried cellulose that is tested in accordance with the United Nations (UN) test protocol for Oxidizers, namely; the protocol found in "Recommendations on the Transport of Dangerous Goods: Manual of Tests and Criteria" 4$^{th}$ Revised Edition, New York, 2003, ST/SG/AC. 10/11/Rev. 4, ISBN 92-1-139087-7, pp. 370-373.

The term "aluminum hydroxide" means unhydrated aluminum hydroxide, CAS No. 21645-51-2.

Calcium hypochlorite is a known and commercially available material. Commercial grades of calcium hypochlorite typically contain at least 39, e.g., at least 45, weight percent free available chlorine. More typically, commercial grades of calcium hypochlorite contain at least 50 or 55 weight percent free available chlorine, such as at least 60 weight percent free available chlorine, e.g., between 60 or 65 and 73 or 80 percent free available chlorine.

Calcium hypochlorite suitable for use in the preparation of the herein described compositions may contain between 45 and 80 weight percent free available chlorine. It should be understood that the compositions of the present invention will have a free available content that is less than the FAC of the starting (unmodified) calcium hypochlorite because of the diluting effect of the added aluminum hydroxide (and any added inorganic salt). Therefore, the FAC content of the starting calcium hypochlorite should be chosen such that the desired FAC content of the final composition is attained while also reaching the desired increase in UN-burn time and/or oxidizer classification.

The calcium hypochlorite useful in the preparation of the herein described novel compositions can contain greater than 50 weight percent, e.g., 55 weight percent, of free available chlorine. Alternatively, the calcium hypochlorite can contain between 50 and 80, such as 65 and 80, or 65 and 73 or 76, or 70 and 80 weight percent free available chlorine. Calcium hypochlorite used to prepare the compositions of the present invention can contain an amount of free available chlorine that ranges between any combination of the described weight percent values, including the recited values.

Particulate, e.g., granular, calcium hypochlorite, typically is prepared by first drying a wet cake comprising calcium hypochlorite dihydrate [$Ca(OCl)_2 \cdot 2H_2O$] crystals and process mother liquor, which usually contains the by-product calcium compounds and alkali metal salts. The dried cake product comprising calcium hypochlorite and interspersed by-product calcium compounds and alkali metal salts is conveyed (after separation of fine airborne dust) to a ribbon compactor for further de-aeration. Thereafter, the compactor ribbon product is broken into granules or grain-like particles, e.g., in a granulator, which granules are processed through shaker screens to produce a finished manufactured granular product having a desired particle size range.

Chemically, the components of thus synthesized (manufactured) particulate calcium hypochlorite (other than the calcium hypochlorite itself) generally comprise varying amounts of water and, as mentioned, varying minor amounts of inorganic by-product calcium compounds and alkali metal salts that are incorporated into the calcium hypochlorite product during its manufacturing process. Such materials can include, but are not limited to, sodium chloride, calcium chloride, calcium hydroxide, calcium carbonate and calcium chlorate.

Water generally comprises between 5.5 and 16 percent by weight of commercial high strength hydrated calcium hypochlorite, e.g., products containing from 65 to 78 weight percent calcium hypochlorite, although amounts less than 5.5 weight percent may be present in dry calcium hypochlorite, e.g., 1 to 2 weight percent. Generally water can comprise 12 percent by weight or less, e.g., 10 percent by weight or less, or 8.5 percent by weight or less of commercially available calcium hypochlorite that is used to prepare the compositions of the present invention. In one example, the amount of water present in hydrated calcium hypochlorite can range between 5.5 and 8.5 or 10 percent, by weight of the hydrated calcium hypochlorite material. The amount of water that is present in calcium hypochlorite can vary between any combination of the specified values, inclusive of the recited values.

The particle size and particle size distribution of particulate, e.g., granular, calcium hypochlorite material used to prepare the compositions of the present invention can vary. Although having some influence on the precise properties of the mixture, such as flowability and caking, the particle size and particle size distribution of the particulate calcium hypochlorite can vary from a powdery to a granular material.

As a general guideline, commercially manufactured particulate calcium hypochlorite (the finished granular product following screening) is a granular material that commonly has a principal size distribution between 100 and 6 mesh, as measured by the American Standard Test Method E11 Alternative Sieve Designation (ASTM E11 ASD); namely, the particles vary in size principally between 0.15 millimeters (mm) (0.006 inches) and 3.35 mm (0.13 inches). Commercially manufactured particulate calcium hypochlorite typically has a principal size distribution between 60 mesh (0.25 mm) and 10 mesh (2.00 mm) or 18 mesh (1.00 mm) based on ASTM E11 ASD. Further, when solid formed articles of the calcium hypochlorite compositions of the present invention are prepared, one skilled in the art will typically select a particle size distribution for the calcium hypochlorite that is amenable to be compressed into the desired solid formed article, e.g., a tablet. An example of commercially manufactured granular calcium hypochlorite that can be used to prepare calcium hypochlorite compositions of the present invention is the product available from PPG Industries, Inc. under the trademarks PITTCLOR® or ZAPPIT™.

Calcium hypochlorite (unmodified), as described herein, typically is present in the compositions of the present invention in amounts at least sufficient to provide a free available chlorine content that would result in such calcium hypochlorite being classified as a DOT Packing Group II oxidizer in the absence of added aluminum hydroxide and any added inert inorganic salts, e.g., alkali metal salts. The calcium hypochlorite can be present in the described compositions in amounts sufficient to provide at least 35%, e.g., 45 or 50%, by weight free available chlorine (FAC), such as from at least 45 to 60% by weight FAC, based on the total composition weight. Also, the calcium hypochlorite can be present in the composition in amounts that provide less than approximately 70% FAC by weight, e.g., less than 65% by weight FAC, based on total composition weight. Compositions prepared in accordance with the present invention can have present therein calcium hypochlorite in an amount sufficient to provide an FAC content ranging between any of those stated values, inclusive of the recited values, e.g., between 35 and 70% by weight FAC, such as between 40 or 45, e.g., 50, or 55 and 65% by weight FAC.

The proportions of calcium hypochlorite and added aluminum hydroxide are chosen so that the resulting composition has an available chlorine content of at least 35 percent and the UN-burn time of the composition is increased by a factor of at least 2.5, or at least 3 compared to the UN-burn time of unmodified calcium hypochlorite. The UN/US Department of Transportation (DOT) classification of the resulting composition is not a Packing Group I or Packing Group II Division 5.1 oxidizer material, but rather is categorized at least as a DOT Packing Group III Division 5.1 oxidizer. The proportions of calcium hypochlorite and added aluminum hydroxide are chosen so that the resulting composition is categorized as a non-Division 5.1 oxidizer.

In accordance with regulations of the US Department of Transportation, 49 CFR §173.127(a), an "oxidizer" (Division 5.1) is defined as a material that may, generally by yielding oxygen, cause or enhance the combustion of other materials. A solid material is classified as a Division 5.1 oxidizer material if, when tested in accordance with the UN Manual of Tests and Criteria, the solid material has a mean burning time that is less than or equal to the burning time of a 3:7 potassium bromate-cellulose mixture [49 CFR §173.127(a)(1)].

Solid Division 5.1 materials are assigned packing groups using the following criteria [49 CFR §173.127(b)]:

(i) Packing Group 1 is the sub-classification of any material which, in the 4:1 or 1:1 sample to cellulose ratio (by mass) tested exhibits a mean burning time less than the mean burning time of a 3:2 mixture, by mass, of potassium bromate and cellulose.

(ii) Packing Group II is the sub-classification of any material which, in the 4:1 or 1:1 sample to cellulose ratio (by mass) tested exhibits a mean burning time less than the mean burning time of a 2:3 mixture, by mass, of potassium bromate and cellulose, and the criteria for Packing Group I are not met.

(iii) Packing Group III is the sub-classification of any material which, in the 4:1 or 1:1 sample to cellulose ratio (by mass) tested exhibits a mean burning time less than the mean burning time of a 3:7 mixture, by mass, of potassium bromate and cellulose, and the criteria for Packing Groups I and II are not met.

A non-Division 5.1 oxidizer material is a material which, in the 4:1 or 1:1 sample to cellulose ratio (by mass) tested, does not ignite and burn, or exhibits a mean burning time greater than that of a 3:7 mixture, by mass, of potassium bromate and cellulose.

The aluminum hydroxide added to the calcium hypochlorite in the compositions of the present invention may be in any useable solid form, e.g., in the form of a powder or in granular form. When formed articles of calcium hypochlorite are contemplated, the solid form of the aluminum hydroxide should not be such as to negatively impact the processing, e.g., compression, of the calcium hypochlorite composition into a desired shape or form, e.g., a tablet.

The amount of aluminum hydroxide added to the calcium hypochlorite to increase substantially the UN-burn time of the resulting mixture or to lower the oxidizer classification of the resulting calcium hypochlorite composition (compared to unmodified calcium hypochlorite) can vary and will depend in part on the chemical make-up of the particular calcium hypochlorite manufactured material used, e.g., the free available chlorine (FAC) and water content of the unmodified calcium hypochlorite. In a non-limiting embodiment of the present invention, the amount of aluminum hydroxide present in the calcium hypochlorite composition is sufficient to increase the UN-burn time of the composition by a factor of at least 2.5, as compared to unmodified calcium hypochlorite. In one example, the UN-burn time is increased by a factor of at least 3.

In one aspect of the invention from 1.5 to 35, e.g., from 10 or 20 to 35, weight percent of aluminum hydroxide is added to the calcium hypochlorite to increase substantially the UN-burn time of the resulting composition and/or to provide a calcium hypochlorite composition having a UN/DOT Packing Group oxidizer classification of at least III. Alternatively the amount of aluminum hydroxide added to the calcium hypochlorite provides a calcium hypochlorite composition that is not a UN/DOT Division 5.1 oxidizer material.

Water-soluble inorganic salt can be added to the blend of calcium hypochlorite and aluminum hydroxide. Such salt(s) are added subsequent to the formation of the particulate, e.g., granular, calcium hypochlorite so that the added salt is appended to the particles, e.g., granules, of calcium hypochlorite that is, the added salt is not distributed internally or within the particles but is physically associated with and external to the particles. The water-soluble inorganic salts that can be added to the calcium hypochlorite compositions of the present invention can vary, but are generally alkali metal salts, e.g., a sodium or potassium salt. The added inorganic salt typically is pH neutral. In one example the inorganic salt is anhydrous; however, it may contain water of hydration if such hydrated water does not deleteriously affect the stability, e.g., the shelf life, of the calcium hypochlorite compositions of the present invention.

The added inorganic salt can be an inert salt that is compatible with the calcium hypochlorite. Non-limiting examples of compatible added inert water-soluble inorganic salts include sodium chloride and potassium chloride. Other inorganic salts that may be used include, but are not limited to, potassium sulfate and sodium sulfate. Mixtures of such inorganic salts can be used. If added, the alkali metal sulfate salts should be added in only minor amounts, e.g., amounts that will not result in the formation (by the metathesis reaction of the alkali metal sulfate and calcium hypochlorite) of destabilizing amounts of calcium sulfate and sodium or potassium hypochlorite, which are not stable in the solid state.

The added inorganic salt such as the compatible, inert alkali metal chlorides can be in any useable solid form, e.g., in the form of a powder, in granular form or in the form of a flake, e.g., flake salt. The form of the salt should not be such as to negatively impact the processing, e.g., compression, of the calcium hypochlorite composition into a shaped form, e.g., a tablet, when formed articles are contemplated. The described inorganic salts are known to those skilled in the art and if not commercially available can be synthesized by known chemical synthesis procedures.

The amount of added water-soluble inorganic salt used can vary. For example, the amount of added inorganic salt used, e.g., the compatible, inert inorganic salt, such as the alkali metal chloride salts can vary from 3 to 15 weight percent, e.g., from 5 to 10 weight percent, based on the weight of calcium hypochlorite in the composition.

The calcium hypochlorite compositions of the present invention can have varying amounts of water of hydration provided by the components of the composition, e.g., principally from the calcium hypochlorite. For example, the amount of water in the calcium hypochlorite composition may vary from 5.5 to 10, e.g., from 5.5 to 8.5, weight percent water.

The calcium hypochlorite compositions of the present invention can be prepared by dry blending at ambient temperatures the calcium hypochlorite and aluminum hydroxide components in any appropriate dry blending vessel by methods known to those skilled in the art, e.g., by tumble mixing of the components, passing the components through a screw conveyer, or by other suitable dry blending methods. The dry blending vessel should be fabricated from materials that are resistant to chemical attack from the components being mixed.

The added inert inorganic salt can be added to particulate manufactured calcium hypochlorite prior to or subsequent to the mixing of the calcium hypochlorite with the aluminum hydroxide. The added inert inorganic salt can be added simultaneously with the added aluminum hydroxide. Alternatively, the aluminum hydroxide and inert inorganic salt are first blended together and this mixture blended with the granular calcium hypochlorite.

To avoid uptake of water by the calcium hypochlorite-aluminum hydroxide/inert inorganic salt mixture from the atmosphere in very humid conditions, the blending of the components should be performed under conditions that substantially exclude atmospheric water. For example, closed blending vessels or nitrogen gas pads can be used to exclude atmospheric water in such circumstances. Such precautions may not be required when low humidity conditions are present and there is little opportunity for the components to absorb substantial amounts of water from the atmosphere. Further, care should be taken during the blending operation to avoid the loss of water from the composition by the use of blending conditions that are too dry, which may cause dehydration of the composition.

The vessel in which the blending process is performed desirably is substantially closed to the atmosphere so that the volume ratio of free air to solid mixture in the vessel is not excessive. The resulting blend generally will be substantially uniform in the distribution of the blended components, but the blend may not be completely homogeneous since there may be some disparity in the distribution of the added components and the solid calcium hypochlorite within the blend due to the blending procedure and/or different sizes of the solid components used to prepare the blend. Further, the mixture may not be entirely homogenous because of the possible separation of portions of the components due to settling, handling, shipping, etc of the blend.

The calcium hypochlorite compositions of the present invention also may contain one or more additives, e.g., adjuvants, that do not affect the shelf life or oxidizer classification of the composition, or that deleteriously affect the sanitizing effectiveness of the composition. In one example, when compositions of the present invention are formed into solid shaped articles, e.g., tablets, adjuvant materials that may be present can include, but are not limited to, conventional binders and buffering agents. Other adjuvants that may be present when the compositions are in either tablet or granular form can include, but are not limited to, chemically compatible scale inhibitors, dyes such as those used for the colorant-containing inorganic salts described in U.S. Pat. No. 5,049,385, at column 5, line 62 through column 7, line 8, and polyfluorinated polymers, such as those described in U.S. Pat. No. 4,970,020 at column 4, line 4 through column 6, line 8, which disclosures are incorporated herein by reference. When colorant-containing inorganic salt is used, the amount of such salt [if it is an inert, water-soluble inorganic salt, i.e., component (c)] should be included in the total amount of inert, water-soluble inorganic salt that is to be added to the blend of calcium hypochlorite and aluminum hydroxide.

The amount of adjuvant materials present within the calcium hypochlorite compositions of the present invention can vary. Generally, such materials can be present in amounts, for example, ranging from 0.001% to 15% by weight, alternatively from 0.01% to 12.5% by weight, e.g., from 0.1 to 5% by weight, based on the total weight of the composition. The amount that each of adjuvant additives that may be present in the calcium hypochlorite compositions of the present invention can vary between any of the aforestated values, inclusive of the recited values. For example, a non-limiting example of such an adjuvant material and its amount can include, but is not limited to, sodium tripolyphosphate, which can be present, for example, in amounts of from 0.25 to 5 weight percent, e.g., 0.9 to 3 weight percent.

Formed calcium hypochlorite articles prepared from the compositions of the present invention can be added directly to an aqueous medium to be treated, e.g., sanitized, or may be added to any suitable chlorination unit or device, which is used to prepare an aqueous solution of calcium hypochlorite, which solution in turn is used to sanitize an aqueous body of water, e.g., a swimming pool, hot tub or spa. Non-limiting examples of suitable chlorination units are those described in FIG. 1 of U.S. Pat. No. 5,384,102, FIG. 1 of U.S. Pat. No. 5,427,748 and FIG. 1 of U.S. Pat. No. 6,298,871 B1, which Figures and the supporting disclosures describing the structures of the chlorination units are incorporated herein by reference.

Calcium hypochlorite compositions of the present invention and formed articles prepared from such compositions are useful for the treatment of standing and recirculating water systems, such as cooling towers, evaporative condensers, air washers, swimming pools, hot tubs, spas, etc, and for the preparation of aqueous calcium hypochlorite solutions useful for sanitizing surfaces. When used to sanitize the surface of an article, the sanitizing water can be applied to such a surface by any appropriate method, examples of which include but are not limited to, spray application, wiping with rags soaked with the sanitizing solution, curtain or waterfall applications, and soaking by immersion.

Compositions of the present invention can be formed into solid shaped articles, including but not limited to, tablets, bricks, briquettes, pellets, etc, by conventional size enlargement equipment. Examples of such equipment include, but are not limited to, molding presses, tableting presses, roll-type presses, pellet mills and screw extruders.

In one example, the solid shaped article can have a mass of between 0.7 gram and 350 grams or more, e.g., between 1 and 325 grams. The mass of the solid shaped article can vary widely and is determined typically by the intended application, such as the internal dimensions and operating parameters of a chlorination unit in which the solid shaped article is to be used, and/or conventional commercial handling and packaging units. The mass of the solid shaped article, e.g., tablet, can be, for example, 0.7, 1, 7, 20, or 140-145, 300, 325 or 350 grams. In the case of a solid shaped article that is formed in the shape of a tablet having a mass of, for example, from 300 to 350 grams, the diameter of the tablet can be, for example, between 7.6 centimeters (cm) (3 inches) and 8.9 cm (3.5 inches), e.g., between 7.9 cm (3.125 inches) and 8.3 cm (3.25 inches), and have a thickness of from 2.5 cm (1 inch) to 5.1 cm (2 inches), e.g., 3.2 cm (1.25 inches). The dimensions of such a tablet can vary between any combination of the aforestated values, inclusive of the recited values.

Granular calcium hypochlorite having a size distribution predominantly between 45 mesh and 10 mesh (ASTM E11 ASD), i.e., the granules are principally between on average 0.36 mm (0.014 inches) and 2.00 mm (0.08 inches), can be used to produce the compositions of the present invention and such compositions are used to produce solid shaped articles, such as tablets. Particles smaller than 50 mesh (ASTM E11 ASD), i.e., 0.30 mm (0.012 inches), that are present in the granular calcium hypochlorite generally represent a minor percentage, usually less than 2 weight percent, of the material charged to a size enlargement device.

The present invention is more particularly described in the examples that follow, which are intended to be illustrative only, since numerous modifications and variations therein will be apparent to those skilled in the art. In the following examples, unless otherwise specified, all parts and percentages are by weight.

In the following examples, the UN-burn time was determined in accordance with the United Nations (UN) Test Method for Division 5.1 Oxidizers, as referenced hereinabove. The test was performed as follows: A sample of the calcium hypochlorite test composition was mixed with cellulose (24 grams of the test composition and 6 grams of cellulose) to form a 30 gram sample. The sample was mechanically mixed as thoroughly as possible without excessive stress and placed in a 60 degree funnel having a 70 mm diameter at its broadest point. The sample (in the shape of a cone or truncated cone) was formed over a 12 inch (30.5 cm) looped nickel/chrome heating wire resting in the center of a 6 inch×6 inch (15.2×15.2 cm) cement board by placing the large section of the funnel over the heating wire on the cement board and removing the funnel. Power (150 Watts) was applied to the heating wire and maintained for the duration of the test or three minutes if the sample did not burn. The test was performed in a ventilated area at atmospheric pressure and ambient temperature (about 20° C.).

The time from the application of electrical current to completion of the visible reaction (or three minutes if no reaction was observed) was recorded as the "burn time" of the sample. The test was performed five times and an average value for the five tests obtained.

For calibration, the average burn time value can be compared to the burn times for various reference mixtures of potassium bromate and cellulose. Typical values reported for these reference mixtures in UN manuals are:

| Potassium Bromate/Cellulose Ratio | Typical Burn Time, Seconds | UN Classification |
|---|---|---|
| 3:7 | 100 | Packing Group III |
| 2:3 | 54 | Packing Group II |
| 3:2 | 4 | Packing Group I |

When the burn (smoldering) time is longer than that of the 3:7 bromate/cellulose mixture, the sample is considered to be a Non-Division 5.1 oxidizer.

EXAMPLE

Samples of the same batch of ZAPPIT granular calcium hypochlorite (69 weight percent available chlorine, predominately 10-60 mesh size) [PPG Industries, Inc.] were each blended separately with various amounts of aluminum hydroxide [$Al(OH)_3$], non-hydrated alumina ($Al_2O_3$), (both obtained from Alcoa Inc.) or Alberger sodium chloride (NaCl) flake salt to yield blends containing various amounts of available chlorine. Each of the blends (24 grams) was mixed with cellulose (6 grams) and the "burn times" for each blend obtained using the UN test protocol described hereinabove. The cellulose used was Whatman grade CF-11, Catalog #4021050 from Whatman International, Maidstone, England, which was pre-dried to constant weight and less than 0.5 percent water and stored in a desiccator until used. Results are tabulated in the following Table.

TABLE

| Available | Wt. % in Blend | | | | Burn Time, |
|---|---|---|---|---|---|
| $Cl_2$, Wt % | Cal Hypo | $Al(OH)_3$ | $Al_2O_3$ | NaCl | Seconds |
| 55 | 79.7 | 20.3 | 0 | 0 | 83 |
| 50 | 72.4 | 27.6 | 0 | 0 | 123 |
| 45 | 65.2 | 34.8 | 0 | 0 | 193 |
| 55 | 79.7 | 0 | 20.3 | 0 | 26 |
| 50 | 72.4 | 0 | 27.6 | 0 | 27 |
| 55 | 79.7 | 0 | 0 | 20.3 | 29 |
| 50 | 72.7 | 0 | 0 | 27.3 | 28 |
| 60 | 87.2 | 0 | 0 | 12.8 | 19 |

Comparable UN burn tests performed with unmodified calcium hypochlorite having a nominal available chlorine content of about 65 percent (PPG Industries, Inc.) yielded average burn times of approximately 9 to 12 seconds.

The data of the foregoing table shows that when appropriate amounts of aluminum hydroxide are blended with unmodified calcium hypochlorite, the UN burn times of the blends are increased substantially. When comparable amounts of alumina or sodium chloride are blended with unmodified calcium hypochlorite, the UN-burn times are significantly shorter.

Although the present invention has been described with reference to specific details of certain embodiments thereof, it is not intended that such details should be regarded as limitations upon the scope of the invention except insofar as they are included in the accompanying claims.

What is claimed is:

1. A solid composition consisting of a mixture of (a) particulate calcium hypochlorite and (b) an amount of aluminum hydroxide sufficient to increase the UN-burn time of the composition by a factor of at least 2.5 compared to that of the calcium hypochlorite, said composition having an available chlorine content of at least 35 weight percent.

2. The composition of claim 1 wherein the UN-burn time is increased by a factor of at least 3.0.

3. The composition of claim 1 wherein the composition has an available chlorine content of from 35 to 70 weight percent.

4. The composition of claim 1 wherein the amount of aluminum hydroxide in the composition is from 1.5 to 35 weight percent.

5. The composition of claim 1 wherein the amount of aluminum hydroxide is from 1.5 to 35 weight percent and the available chlorine content of the composition is from 35 to 65 weight percent.

6. The composition of claim 1 wherein the amount of aluminum hydroxide present in the composition is from 10 to 35 weight percent, the available chlorine content is from 35 to 65 weight percent and the UN-burn time is increased by a factor of at least 3.0.

7. A solid composition consisting of a mixture of (a) granular calcium hypochlorite having a UN Packing Group oxidizer classification of II and (b) an amount of aluminum hydroxide such that the composition is classified as a Packing Group III Division 5.1 oxidizer or as a non-Division 5.1 oxidizer, said composition having an available chlorine content of at least 40 weight percent.

8. The composition of claim 7 wherein the amount of aluminum hydroxide present in the composition is from 10 to 35 weight percent, and wherein the composition has an available chlorine content of from 45 to 65 weight percent.

9. A solid composition consisting of a mixture of (a) particulate calcium hypochlorite, (b) an amount of aluminum hydroxide sufficient to increase the UN-burn time of the composition by a factor of at least 2.5 compared to that of the calcium hypochlorite, and (c) added inert water-soluble inorganic salt other than aluminum hydroxide that is compatible with the calcium hypochlorite and that is appended to and external of the particles of the particulate calcium hypochlorite, said composition having an available chlorine content of at least 35 weight percent.

10. The composition of claim 9 wherein the water-soluble inorganic salt is present in an amount of from 3 to 15 weight percent, based on the amount of calcium hypochlorite in the composition.

11. The composition of claim 10 wherein the amount of aluminum hydroxide present in the composition is from 10 to 35 weight percent, and the added inert, water-soluble inorganic salt is chosen from sodium chloride, potassium chloride and mixtures of such salts.

12. The composition of claim 11 wherein the added inert, water-soluble inorganic salt is sodium chloride.

13. A solid composition consisting of a mixture of (a) granular calcium hypochlorite having a UN Packing Group oxidizer classification of II, (b) an amount of aluminum hydroxide such that the composition is classified as a Packing Group III Division 5.1 oxidizer or as a non-Division 5.1 oxidizer, and (c) added compatible inert, water-soluble inorganic salt other than aluminum hydroxide that is appended to the granules of the granular calcium hypochlorite, said composition having an available chlorine content of at least 40 weight percent.

14. The composition of claim 13 wherein the water-soluble inorganic salt is present in an amount of from 3 to 15 weight percent based on the amount of calcium hypochlorite in the composition and is chosen from sodium chloride, potassium chloride and mixtures of such salts.

15. A solid shaped article comprising an article formed from a calcium hypochlorite composition consisting of a mixture of (a) particulate calcium hypochlorite having a UN Packing Group oxidizer classification of II and (b) an amount of aluminum hydroxide such that the calcium hypochlorite composition is classified as a Packing Group III Division 5.1 oxidizer or as a non-Division 5.1 oxidizer, said composition having an available chlorine content of at least 40 weight percent.

16. The solid shaped article of claim 15 wherein the amount of aluminum hydroxide present in the composition is from 10 to 35 weight percent and the available chlorine content of the composition is from 45 to 65 weight percent.

17. The composition-solid shaped article of claim 16 wherein the article is in a form chosen from tablets, bricks, briquettes and pellets.

18. A solid shaped article comprising an article formed from a calcium hypochlorite composition consisting of a mixture of (a) particulate calcium hypochlorite having a UN Packing Group oxidizer classification of II, (b) an amount of aluminum hydroxide such that the calcium hypochlorite composition is classified as a Packing Group III Division 5.1 oxidizer or as a non-Division 5.1 oxidizer, and (c) added compatible inert water-soluble inorganic salt other than aluminum hydroxide that is appended to the particles of the calcium hypochlorite, said composition having an available chlorine content of at least 40 weight percent.

19. The solid shaped article of claim 18 wherein the amount of aluminum hydroxide present in the composition is from 10 to 35 weight percent and the available chlorine content of the composition is from 45 to 65 weight percent.

20. The solid shaped article of claim 19 wherein the water-soluble inorganic salt is present in an amount of from 3 to 15 weight percent based on the amount of calcium hypochlorite in the composition and is chosen from sodium chloride, potassium chloride and mixtures of such salts.

21. The solid shaped article of claim 20 wherein the article is in a form chosen from tablets, bricks, briquettes and pellets.

22. The solid shaped article of claim 18 wherein the shaped article is in the form of a tablet having a mass of between 0.7 and 350 grams.

* * * * *